United States Patent [19]

Walser et al.

[11] Patent Number: 4,677,121
[45] Date of Patent: Jun. 30, 1987

[54] METHOD OF INHIBITING MUSCLE PROTEIN DEGRADATION

[75] Inventors: Mackenzie Walser, Ruxton; Daniel G. Sapir, Baltimore, both of Md.; Peter M. Stewart, Sydney, Australia

[73] Assignee: The Johns Hopkins University, Baltimore, Md.

[21] Appl. No.: 793,724

[22] Filed: Oct. 31, 1985

Related U.S. Application Data

[63] Continuation of Ser. No. 693,325, Jan. 22, 1985, abandoned, which is a continuation of Ser. No. 366,256, Apr. 7, 1982, abandoned.

[51] Int. Cl.$^4$ .......................................... A61K 31/195
[52] U.S. Cl. .................................. 514/561; 514/869; 514/893; 514/907
[58] Field of Search ................ 514/561, 869, 893, 907

[56] References Cited

U.S. PATENT DOCUMENTS

| | | | |
|---|---|---|---|
| 4,100,160 | 7/1978 | Walser I | 424/317 |
| 4,100,161 | 7/1978 | Walser II | 424/317 |
| 4,100,293 | 7/1978 | Walser III | 424/317 |
| 4,228,099 | 10/1980 | Walser | 514/561 |
| 4,296,127 | 10/1981 | Walser | 514/516 |
| 4,320,146 | 3/1982 | Walser | 514/516 |

OTHER PUBLICATIONS

Stewart, Peter M., Walser, Mackenzie and Drachman, Daniel B., "Branched—Chain Ketoacids Reduce Muscle Protein Degradation in Duchenne Muscular Dystrophy", *Muscle & Nerve,* Mar. 1982, pp. 197–201.
Mitch et al., Nitrogen Sparing Induced by Leucine Compared with that Heat Induced by its Keto Analog, α-Ketoisocaproate, *J. Clin. Inv.* 67:553–12, 1981.
Tischler et al., Relationship of Leucine Catabolism to its Regulatory Effectsion Protein Turnover in Muscle, Fed Proc. 39:1682, 1980.

*Primary Examiner*—Johnnie R. Brown
*Assistant Examiner*—John W. Rollins, Jr.
*Attorney, Agent, or Firm*—Panitch Schwarze Jacobs & Nadel

[57] ABSTRACT

Muscle protein breakdown or degradation may be reduced or inhibited in mammals, particularly humans recovering from surgery or suffering from a muscle wasting disorder, by administering daily doses of alpha-ketoisocaproic acid (ketoleucine) or an appropriate salt of the acid. Seventy millimoles per day of sodium alpha-ketoisocaproate administered for five days after major abdominal surgery was found to significantly reduce urinary 3-methylhistidine/creatinine, which is a measure of muscle protein breakdown, and thereby to improve nitrogen balance.

8 Claims, No Drawings

METHOD OF INHIBITING MUSCLE PROTEIN DEGRADATION

STATEMENT OF GOVERNMENT INTEREST

The invention described herein was made in part in the course of work under a grant or award from the United States Public Health Service, National Institutes of Health.

CROSS-REFERENCE TO RELATED APPLICATIONS

This application is a continuation of U.S. application Ser. No. 693,325, filed Jan. 22, 1985 now abandoned, which is a continuation of U.S. application Ser. No. 366,256, filed Apr. 7, 1982 now abandoned.

BACKGROUND OF THE INVENTION

The present invention is directed to a method of inhibiting or reducing muscle protein degradation in mammals. More particularly, the invention is directed to a method of reducing the breakdown of muscle protein in human patients recovering from surgery or suffering from a muscle wasting disorder.

Various disorders and conditions are characterized by protein wasting or depletion. Such disorders or conditions are often referred to as "nitrogen wasting" diseases or conditions because the patient's nitrogen balance is negative as a result of protein depletion. Such conditions occur in diseases such as malnutrition, uremia, liver disease, cancer, diabetes, sepsis (chronic infection) as well as resulting from such events as burns, surgery, trauma, etc.

Protein depletion may occur because of an unusually high rate of protein degradation or an unusually low rate of protein synthesis, or a combination of both. Thus, if the rate of protein degradation in the body is normal, but protein synthesis is impaired so that the degraded protein is not replaced by newly synthesized protein, protein depletion will occur. Similarly, where protein synthesis is normal, protein may still be depleted if the rate of protein degradation is unusually high due to some disease or condition. Still further, both the rates of protein synthesis and protein degradation in the body may be abnormally high or low to such an extent that the normal nitrogen balance is disturbed and the net result is protein depletion or nitrogen wasting.

Numerous attempts have been made to control one or both of these mechanisms in various disorders in order to conserve nitrogen and prevent protein depletion. For example, U.S. Pat. Nos. 4,100,160; 4,100,161 and 4,100,293 of Mackenzie Walser and assigned to The Johns Hopkins University disclose various treatments for promoting protein synthesis and conserving protein (nitrogen), particularly in patients suffering from renal and hepatic disorders, by the administration of various combinations of essential amino acids with keto and/or hydroxy analogs of certain of the essential amino acids. In addition, U.S. Pat. No. 4,100,161 describes and claims compositions for promoting protein synthesis and conserving nitrogen in patients on protein-restricted diets using a composition consisting of a mixture of the keto-acid analogs of the branched chain essential amino acids valine, leucine and isoleucine.

U.S. Pat. Nos. 4,228,099 and 4,320,146 of Mackenzie Walser describe the use of ornithine and arginine salts of alpha keto analogs of branched chain essential amino acids, particularly arginine alpha-ketoisocaproate and ornithine alpha-ketoisocaproate for promoting protein synthesis by improving nitrogen balance in the treatment of liver disease. Still further, U.S. Pat. No. 4,296,127 of Mackenzie Walser discloses that mixed salts of essential or semi-essential amino acids and nitrogenfree analogs thereof may be useful in the treatment of nitrogen wasting disorders and protein malnutrition.

More recently, it has been found that branched chain keto acids, particularly the ornithine salts, including a major portion of the alpha-ketoisocaproate and smaller amounts of the keto-analogs of valine and isoleucine, have a significant effect in reducing muscle protein degradation in Duchenne muscular dystrophy, a disease in which the rate of synthesis and degradation of muscle protein are both greatly accelerated. P. M. Stewart et al. "Branched-Chain Keto Acids Reduce Muscle Protein Degradation In Duchenne Muscular Dystrophy", *Muscle And Nerve*, Pages 197–201 (March 1982). Branched-chain keto acids, especially alpha-ketoisocaproate, have also been found to spare nitrogen (reduce protein wastage) in fasting obese subjects. W. E. Mitch et al., "Nitrogen Sparing Induced By Leucine Compared With That Induced By Its Keto Analog, Alpha-Ketoisocaproate, In Fasting Obese Man", *Journal of Clinical Investigation*, Volume 67, Pages 553–562 (February 1981). Still further, it has been reported that whereas leucine itself probably stimulates the synthesis of muscle protein in vitro, alpha-ketoisocaproic acid (ketoleucine) in vitro inhibits muscle protein breakdown without stimulating protein synthesis. The latter studies were based on isolated rat diaphragms and atria. M. E. Tischler et al., "Relationship Of Leucine (Leu) Catabolism To Its Regulatory Effects On Protein Turnover In Muscle", *Federation Proceedings* (Federation of American Societies for Experimental Biology) Vol. 39, Page 1682 (May 1980).

Despite the latter reports of Mitch et al. and Tischler et al., leucine has not been found to reduce muscle protein degradation in vivo, nor has it been found to promote protein synthesis or reduce muscle protein degradation in obese men. Hence, in view of the complete conversion of leucine to ketoleucine in the body, no advantage has been seen to administering ketoleucine in muscle wasting disorders or conditions.

BRIEF SUMMARY OF THE INVENTION

It has now been found that the degradation of muscle protein may be inhibited or reduced by the administration to patients of a composition consisting essentially of alpha-ketoisocaproic acid or pharmaceutically acceptable salts thereof. Daily administration of this composition, for example after surgery, significantly reduces the presence of 3-methylhistidine/creatinine in the urine. The composition may be administered by intravenous infusions.

DETAILED DESCRIPTION OF PREFERRED EMBODIMENTS

Surgery is followed by increased muscle protein breakdown and reduced plasma levels of liver-synthesized proteins. Conventional post-operative treatment consists of daily intravenous infusions of 10 grams of glucose and 70 millimoles of sodium bicarbonate for several days after surgery.

The rate of degradation of muscle protein is manifested by the rate of urinary excretion of 3-methylhistidine. This amino acid resides almost exclusively in muscle protein and is released when protein is degraded. It is quantitatively excreted into the urine and is therefore generally accepted as a valid measure of muscle protein degradation in subjects who are not consuming meat.

According to the present invention, it has been found that the intravenous administration of alpha-ketoisocaproic acid reduces muscle protein breakdown and urea nitrogen excretion in patients recovering from surgery. The invention is also useful in the treatment of diseases or conditions where there is a disparity in the rates of muscle protein synthesis and degradation such that the net effect is depletion of muscle protein. These include both primary muscle diseases which involve accelerated degradation or defective synthesis or both, such as malnutrition, muscular dystrophy, uremia, etc. and conditions which secondarily involve muscle protein breakdown, such as burns, surgery, trauma, etc.

This result is quite unexpected in that leucine itself, administered under the same conditions, does not reduce muscle protein breakdown. Since leucine converts in the body to its keto analog, namely alpha-ketoisocaproic acid (ketoleucine), it was not expected that ketoleucine would have any effect in reducing muscle protein degradation since leucine itself had no effect. Moreover, according to the invention it is not necessary to include in the composition other essential amino acids and/or keto analogs thereof, such as the other branched chain amino (keto) acids valine (alpha-ketoisovaleric acid) or isoleucine (alpha-keto-beta-methylvaleric acid).

Alpha-ketoisocaproic acid is the alpha-keto analog of the branched chain essential amino acid leucine. This acid may be prepared from the calcium salt of the keto analog which is available commercially from REXIM of Paris, France. The calcium salt is suspended in water to form a slurry to which is added an excess of hydrochloric acid. The resulting clear solution is then filtered, and the filtrate is extracted with ether. The ether extract, which contains the free acid, is then removed and subjected to evaporation at reduced pressure and 30° C. Evaporation of the ether leaves behind the free keto acid, which is a liquid.

Instead of using the free acid, compositions of the present invention may be prepared from pharmaceutically acceptable salts of the keto acid, such as sodium or calcium salts or acid salts such as ornithine, arginine, lysine or histidine salts. Intravenous infusions for use in the present invention may be prepared simply by dissolving the acid or one of its salts in water, usually in concentrations of about 70 millimoles of the salt per 500 ml (140 mmoles/liter). Other concentrations and dosages may be used depending upon the patient and condition being treated, as will be recognized by those of ordinary skill in the art in view of this disclosure.

The invention will now be described in more detail with reference to the following specific, non-limiting example:

21 adults scheduled for elective major abdominal surgical operations were randomized into three groups of seven each (after obtaining their informed consent). Group I received daily (4 hour) intravenous infusions of 10 gm of glucose plus 70 mmoles NaHCO$_3$ on the day of surgery and the subsequent four days. Group II received daily infusions on these same days of leucine, 70 mmoles, plus NaHCO$_3$, 70 mmoles. Group III received daily infusions on these same days of sodium alpha-ketoisocaproate, 70 mmoles. No other glucose or other energy source was administered and the patients received nothing by mouth during these five days.

The rate of degradation of muscle protein was estimated from the rate of urinary excretion of 3-methylhistidine. The measured rate of 24 hr urinary 3-methylhistidine was factored by the simultaneous rate of urinary excretion of creatinine in order to correct for possibly incomplete urine collections and in order to normalize the results of varying body size.

Average values for the four post-operative days for urinary 3-methylhistidine in μmol per gm of creatinine in the three groups were as follows (these are all higher than usual normal values):

| Group | Post Operative Day | | | | |
|---|---|---|---|---|---|
| | 1 | 2 | 3 | 4 | Mean |
| I | 300 | 308 | 304 | 309 | 305 |
| II | 248 | 333 | 351 | 390 | 330 |
| III | 219 | 208 | 224 | 207 | 214 |

The difference between Group III and the other two groups is statistically significant on days 2, 3, and 4, as well as the four-day mean. Thus sodium alpha-ketoisocaproate significantly reduces muscle protein degradation by about ⅓ in post-operative patients, as compared with isocaloric quantities of glucose or leucine (given with sodium bicarbonate).

Nitrogen balances were measured in these same subjects by 24-hr urine nitrogen determination (corrected per gm of creatinine as above), determination of nitrogen in gastric drainage (if any), and allowance for N taken in as leucine in Group II (1 gm/day). Stool N is virtually zero in such patients. The results are shown as four-day mean negative N balance:

| Group | N balance, gm/day |
|---|---|
| I | −6.53 |
| II | −6.28 |
| III | −5.01 |

The result in Group III is statistically significantly different from Group II or Group I.

Thus sodium alpha-ketoisocaproate attenuates the negative N balance of post-operative patients, as compared with glucose or leucine. The probable mechanism of this effect is the reduction in muscle protein breakdown.

The present invention may be embodied in other specific forms without departing from the spirit or essential attributes thereof and, accordingly, reference should be made to the appended claims, rather than to the foregoing specification as indicating the scope of the invention.

We claim:

1. A method of reducing muscle protein degradation in patients suffering from such degradation comprising administering to said patient an effective amount of a composition consisting essentially of alpha-ketoisocaproic acid or a pharmaceutically acceptable salt thereof.

2. A method according to claim 1 wherein the patient is recovering from surgery.

3. A method according to claim 2 wherein sodium alpha-ketoisocaproate is administered in an amount of about 70 millimoles per day.

4. A method according to claim 1 wherein the patient is suffering from a muscle wasting disorder.

5. A method according to claim 1 wherein the salt of alpha-ketoisocaproic acid is sodium alpha-ketoisocaproate.

6. A method according to claim 1 wherein said composition is in the form of a solution which is administered intravenously.

7. A method according to claim 1 wherein the patient is suffering from a condition or disease where there is a disparity between the rates of muscle protein synthesis and muscle protein degradation.

8. A method according to claim 7 wherein the patient is suffering from accelerated muscle protein degradation.

* * * * *